United States Patent [19]
Fornasari et al.

[11] Patent Number: 5,527,978
[45] Date of Patent: *Jun. 18, 1996

[54] PROCESS AND CATALYST FOR CONVERTING METHANE INTO HIGHER HYDROCARBON PRODUCTS

[75] Inventors: Giuseppe Fornasari, Cremona; Giuseppe Bellussi, Piacenza, both of Italy

[73] Assignee: Eniricerche S.p.A., Milan, Italy

[*] Notice: The term of this patent shall not extend beyond the expiration date of Pat. No. 5,321,188.

[21] Appl. No.: 142,004

[22] Filed: Oct. 28, 1993

[30] Foreign Application Priority Data

Oct. 30, 1992 [IT] Italy ................... MI92A2488

[51] Int. Cl.⁶ ................................................ C07C 2/00
[52] U.S. Cl. .................. 585/500; 585/700; 585/943; 585/654; 585/656; 585/658; 585/520; 585/530
[58] Field of Search ................... 585/500, 700, 585/943, 654, 656, 658, 520, 530

[56] References Cited

U.S. PATENT DOCUMENTS 5,321,188  6/1994  Fornasari et al. ............... 585/500

FOREIGN PATENT DOCUMENTS 0196541  10/1986  European Pat. Off. .
0492695   7/1992  European Pat. Off. .

OTHER PUBLICATIONS

Industrial & Engineering Chemistry Research, vol. 27, No. 9, Sep. 1988, pp. 1577–1582, Jeffrey M. DeBoy, et al., "The Oxidative Coupling of Methane Over Alkali, Alkaline Earth, and Rare Earth Oxides".

*Primary Examiner*—E. Rollins Cross
*Assistant Examiner*—E. D. Irzinski
*Attorney, Agent, or Firm*—Oblon, Spivak, McClelland, Maier & Neustadt

[57] ABSTRACT

Methane is converted into higher hydrocarbon products by oxidative coupling, by bringing a gaseous mixture containing methane and oxygen into contact with a solid catalyst formed from calcium oxide, magnesium oxide, a lanthanide oxide plus possibly lithium oxide, wherein:
  the lithium content is between 0 and 0.20 wt %,
  the calcium/magnesium atomic ratio is between 0.08 and 0.7, and
  the (calcium+magnesium)/lanthanide atomic ratio is between 0.8/1 and 8/1, and preferably between 2/1 and 4/1.

13 Claims, 4 Drawing Sheets

PROCESS AND CATALYST FOR CONVERTING METHANE INTO HIGHER HYDROCARBON PRODUCTS

This invention relates to the conversion (oxidative coupling) of methane into higher hydrocarbons, and to a selective, active, long-life catalyst for this conversion.

Processes and catalysts are under development in the art for converting methane into higher hydrocarbon products for use as chemicals or energy carriers, or useful as products enabling the drawbacks connected with methane transportation from remote areas to be reduced.

Of the proposed processes, particular attention has been given to oxidative coupling by which in the presence of an oxidizing agent the methane is converted at high temperature into higher hydrocarbons, particularly ethane and ethylene, over suitable catalysts. The oxidizing agent generally used for this purpose is oxygen or air. Catalysts which exhibit activity in methane oxidative coupling processes are generally formed from metal oxides, and in particular are known catalysts containing oxides of transition metals or metals such as lead, bismuth, tin or antimony, catalysts in the form of strongly basic oxides such as magnesia or calcium oxides doped with alkaline metals, or catalysts containing rare earths. For this known art reference should be made to the descriptions of U.S. Pat. Nos. 4,499,322, 4,499,323, 4,499,324 and 4,495,374, and to EP applications 177327 and 230769.

According to a first aspect of the present invention, we have now discovered a catalyst active in methane oxidative coupling processes consisting of calcium oxide, magnesium oxide and a lanthanide oxide, which is characterised by considerable stability.

This catalyst has a performance which remains unaltered for unexpectedly long periods of time.

With regard to methane oxidative coupling processes, the technical and patent literature also describes catalysts containing an alkaline metal oxide, an alkaline-earth metal oxide, plus possibly one or more transition or rare earth metal oxides (Z. K. Bi Yingli et al. Applied Catalysis, 39 [1988] pp 185–190, EP 196,541 and U.S. Pat. No. 4,728, 636). If the alkaline metal is lithium, these catalysts have high initial activity in methane oxidative coupling processes, but this activity unfortunately falls off rapidly with time because of the loss of lithium from the catalyst.

IT 22483 A/90 describes the possibility of preventing or at least reducing the phenomenon of deactivation following lithium loss in certain methane oxidative coupling catalysts by particular expedients used during catalyst preparation. This catalyst, formed from lithium oxide, magnesium oxide and a lanthanide oxide, is basically characterised by a lithium content of less than 0.20%, this being achieved by preparing a mixture of lithium, magnesium and lanthanide oxides in which the lithium content exceeds 1 wt %, then reducing this content in the mixture to less than 0.20 wt % by thermal treatment at high temperature, conducted at least partly in an oxidizing atmosphere.

This catalyst results in high methane conversion and high selectivity of the methane converted into higher hydrocarbons. According to a second aspect of the present invention, we have now discovered that by partially replacing the magnesium with calcium in this catalyst, a more stable catalyst is obtained in the sense of providing improved performance for unexpectedly long periods of time.

In accordance therewith, for converting methane into hydrocarbon products the present invention provides solid catalysts formed from calcium oxide, magnesium oxide, a lanthanide oxide plus possibly lithium oxide, wherein:

the lithium content is between 0 and 0.20 wt. %, the calcium/magnesium atomic ratio is between 0.08 and 0.7, and the (calcium+magnesium)/lanthanide atomic ratio is between 0.8/1 and 8/1, and preferably between 2/1 and 4/1.

In particular, if the catalyst is formed from calcium oxide, magnesium oxide and a lanthanide oxide, the calcium/magnesium atomic ratio is preferably between 0.2 and 0.4. The lanthanide is preferably chosen from neodymium and lanthanum. If the catalyst is formed from calcium oxide, magnesium oxide, a lanthanide oxide and lithium oxide it is produced by:

preparing a mixture of lithium oxide, calcium oxide, magnesium oxide and a lanthanide oxide in which the lithium content exceeds 1 wt %; and reducing the lithium content in the mixture to less than 0.2 wt % by thermal treatment at high temperature, conducted at least partly in an oxidizing atmosphere.

In the preferred embodiment the lithium content of the initial oxide mixture is between 4 and 10 wt % and the lithium content is reduced to a value of the order of 0.1 wt % in the final catalyst. The metal oxide mixture of high lithium content, constituting the catalyst precursor, can be obtained from water-soluble compounds of lithium, calcium, magnesium and the lanthanide by using the sol-gel method or the impregnation methods.

If the sol-gel method is used the procedure is as follows:

an aqueous and/or alcoholic solution of a soluble calcium, magnesium and lanthanide compound is prepared, an aqueous and/or alcoholic solution of the lithium compound and an organic base is prepared, the two solutions are mixed together to form a gel, the gel obtained is dried.

If the impregnation method is used, the procedure comprises preparing a precipitate comprising calcium oxide, magnesium oxide and the lanthanide oxide, then impregnating these oxides with a lithium compound.

The lanthanide compounds which can be used for this purpose are its organic acid salts such as acetates, inorganic salts such as nitrates, and organo-metallic derivatives such as alkoxides. The calcium and magnesium compounds which can be used for this purpose are conveniently chosen from their aliphatic organic acid salts, especially acetates. The lithium compounds can be chosen from lithium hydroxide and lithium carbonate. The catalyst precursor obtained in this manner is subjected to thermal treatment at high temperature, conducted at least partly in an oxidizing atmosphere, to reduce the lithium content to less than 0.20 wt % and preferably of the order of 0.1 wt %. For this purpose the catalyst can be heated in an oxygen stream or in an oxygen-containing gas stream, to a temperature generally of between 700 and 900° C., for a time generally of between 3 and 30 hours.

According to a further embodiment the lithium is partly eliminated from the precursor under the aforesaid oxidizing conditions and is then reduced to the desired value in the presence of methane and oxygen, operating at a temperature of the order of 700°–800° C.

If the catalyst of the present invention is formed from calcium oxide, magnesium oxide and a lanthanide oxide, the catalyst stability still remains unchanged for an unexpectedly long period of time, and even though the catalyst exhibits lesser activity than analogous catalysts containing lithium, it no longer requires a complex preparation procedure. In accordance therewith the catalyst not containing lithium is produced by:

preparing a mixture of calcium oxide, magnesium oxide and a lanthanide oxide, drying this mixture and heating it to high temperature in an oxidizing atmosphere.

The present invention further provides a process for converting methane into higher hydrocarbon products using the aforedescribed catalyst. This is used in the form of a fixed bed to which a gaseous stream containing methane and oxygen, possibly diluted with an inert gas, is fed in a molar methane/oxygen ratio of between 1.5/1 and 12/1 and preferably between 2/1 and 7/1. The oxygen can be fed in pure form or as air or oxygen-enriched air. The process can also be operated under pressure, but is preferably operated without applying higher than atmospheric pressure, at a temperature generally of between 650 and 000° C. and preferably of the order of 800°–950° C., using a short contact time generally of the order of 0.0005–0.02 minutes per gram of catalyst per milliliter of feed gas.

In conclusion, if the catalyst of the present invention contains lithium in a quantity of less than 0.20%, improved methane conversion and improved selectivity of methane converted into higher hydrocarbons are achieved compared with catalysts of the known art, and for unexpectedly lengthy periods of time; if the catalyst of the present invention does not contain lithium it exhibits a lesser activity but a greater stability for an unexpectedly lengthy time, and in addition its synthesis procedure is simpler than that of analogous catalysts containing lithium.

Figure 1:
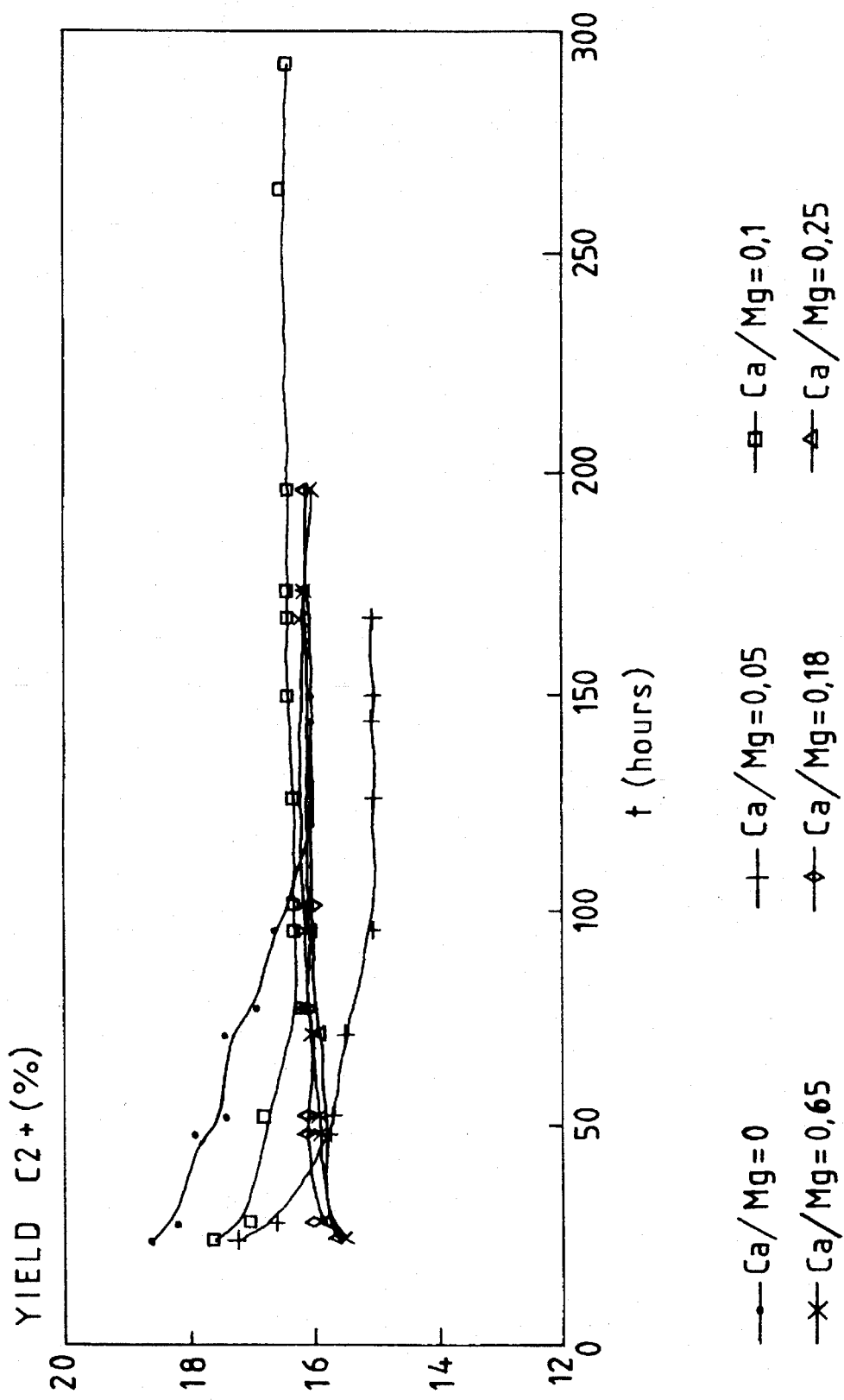
FIGS. 1–4 represent the percent yield of product produced over time for various catalysts being employed in processes as set forth specifically in the following examples.

The following experimental examples are provided to better illustrate the present invention.

EXAMPLE 1

13.6 g of $Mg(CH_3COO)_2 \cdot 4H_2O$ and 0.787 g of $Ca(NO_3)_2 \cdot 4H_2O$ are dissolved in a beaker containing 15 g of $H_2O$ acidified with 0.5 ml of $HNO_3$ (65 wt %). After further acidification with 1.5 ml of $HNO_3$ (65 wt %), 10.9 g of $Nd(CH_3COO)_3 \cdot xH_2O$ and 65 g of $H_2O$ are added (solution A).

A second solution (solution B) is prepared containing 20 g of $H_2O$, 1.6 g of LiOH and 2.25 g of TPAOH (tetrapropyl ammonium hydroxide) (53 wt %).

Solution B is added to solution A under agitation at ambient temperature and homogenized for 15 minutes. In the resultant solution the Li:Ca:Mg:Nd atomic ratio is 40:2:38:20 (Ca/Mg=0.05). The partly gelled solution is left standing for 16 hours. The product obtained is dried at 120° C. for 5 hours to obtain a metal oxide mixture (lithium content 5.0 wt %) which is heated to 800° C. for 4 hours in an air stream. It is then cooled to obtain a solid with a lithium content of about 3.3 wt %.

EXAMPLE 2

12.87 g of $Mg(CH_3COO)_2 \cdot 4H_2O$ and 1.57 g of $Ca(NO_3)_2 \cdot 4H_2O$ are dissolved in a beaker containing 15 g of $H_2O$ acidified with 0.5 ml of $HNO_3$ (65 wt %). After further acidification with 1.5 ml of $HNO_3$ (65 wt %), 10.9 g of $Nd(CH_3COO)_3 \cdot xH_2O$ and 65 g of $H_2O$ are added (solution A).

A second solution (solution B) is prepared containing 20 g of $H_2O$, 1.6 g of LiOH and 2.25 g of TPAOH (tetrapropyl ammonium hydroxide) (53 wt %).

Solution B is added to solution A under agitation at ambient temperature and homogenized for 15 minutes. In the resultant solution the Li:Ca:Mg:Nd atomic ratio is 40:4:36:20 (Ca/Mg=0.1). The partly gelled solution is left standing for 16 hours. The product obtained is dried at 120° C. for 5 hours to obtain a metal oxide mixture (lithium content 5.0 wt %) which is heated to 800° C. for 4 hours in an air stream. It is then cooled to obtain a solid with a lithium content of about 3.2 wt %.

EXAMPLE 3

12.15 g of $Mg(CH_3COO)_2 \cdot 4H_2O$ and 2.36 g of $Ca(NO_3)_2 \cdot 4H_2O$ are dissolved in a beaker containing 15 g of $H_2O$ acidified with 0.5 ml of $HNO_3$ (65 wt %). After further acidification with 1.0 ml of $HNO_3$ (65 wt %), 10.9 g of $Nd(CH_3COO)_3 \cdot xH_2O$ and 65 g of $H_2O$ are added (solution A).

A second solution (solution B) is prepared containing 20 g of $H_2O$, 1.6 g of LiOH and 2.25 g of TPAOH (tetrapropyl ammonium hydroxide) (53 wt %).

Solution B is added to solution A under agitation at ambient temperature and homogenized for 15 minutes. In the resultant solution the Li:Ca:Mg:Nd atomic ratio is 40:6:34:20 (Ca/Mg=0.18).

The partly gelled solution is left standing for 16 hours. The product obtained is dried at 120° C for 5 hours to obtain a metal oxide mixture (lithium content 5.0 wt %) which is heated to 800° C. for 4 hours in an air stream. It is then cooled to obtain a solid with a lithium content of about 3.4 wt %.

EXAMPLE 4

11.44 g of $Mg(CH_3COO)_2 \cdot 4H_2O$ and 3.15 g of $Ca(NO_3)_2 \cdot 4H_2O$ are dissolved in a beaker containing 15 g of $H_2O$ acidified with 0.5 ml of $HNO_3$ (65 wt %). After further acidification with 1.0 ml of $HNO_3$ (65 wt %), 10.9 g of $Nd(CH_3COO)_3 \cdot xH_2O$ and 65 g of $H_2O$ are added (solution A).

A second solution (solution B) is prepared containing 20 g of $H_2O$, 1.6 g of LiOH and 2.25 g of TPAOH (tetrapropyl ammonium hydroxide) (53 wt %).

Solution B is added to solution A under agitation at ambient temperature and homogenized for 15 minutes. In the resultant solution the Li:Ca:Mg:Nd atomic ratio is 40:8:32:20 (Ca/Mg=0.25). The partly galled solution is left standing for 16 hours. The product obtained is dried at 120° C. for 5 hours to obtain a metal oxide mixture (lithium content 5.0 wt %) which is heated to 800° C. for 4 hours in an air stream. It is then cooled to obtain a solid with a lithium content of about 3.1 wt %.

EXAMPLE 5

8.58 g of $Mg(CH_3COO)_2 \cdot 4H_2O$ and 6.30 g of $Ca(NO3)_2 \cdot 4H_2O$ are dissolved in a beaker containing 15 g of $H_2O$ acidified with 0.5 ml of $HNO_3$ (65 wt %). After further acidification with 0.5 ml of $HNO_3$ (65 wt %), 10.9 g of $Nd(CH_3COO)_3 \cdot xH_2O$ and 65 g of $H_2O$ are added (solution A).

A second solution (solution B) is prepared containing 20 g of $H_2O$ 1.6 g of LiOH and 2.25 g of TPAOH (tetrapropyl ammonium hydroxide) (53 wt %).

Solution B is added to solution A under agitation at ambient temperature and homogenized for 15 minutes, In the resultant solution the Li:Ca:Mg:Nd atomic ratio is 40:16:24:20 (Ca/Mg=0.65). The partly gelled solution is left standing for 16 hours.

The product obtained is dried at 120° C. for 5 hours to obtain a metal oxide mixture (lithium content 5.0 wit) which is heated to 00° C for 4 hours in an air stream. It is then cooled to obtain a solid with a lithium content of about 3.4 wt %.

EXAMPLE 6

12.57 g of $Mg(CH_3COO)_2.4H_2O$ and 1.87 g of $Ca(NO_3)_2.4H_2O$ are dissolved in a beaker containing 15 g of $H_2O$ acidified with 0.5 ml of $HNO_3$ (65 wt %). After further acidification with 1.5 ml of $HNO_3$ (65 wt %), 10.9 g of $Nd(CH_3COO)_3.xH_2O$ and 65 g of $H_2O$ are added (solution A).

A second solution (solution B) is prepared containing 20 g of $H_2O$ and 4.00 g of TPAOH (tetrapropyl ammonium hydroxide) (53 wt %). Solution B is added to solution A under agitation at ambient temperature and homogenized for 15 minutes. In the resultant solution the Ca:Mg:Nd atomic ratio is 6.6:60:33.3 (Ca/Mg =0.1). The product obtained is dried at 120° C. for 8 hours and is then heated to 800° C. for 4 hours in an air stream.

EXAMPLE 7

11.44 g of $Mg(CH_3COO)_2.4H_2O$ and 3.15 g of $Ca(NO_3)_2.4H_2O$ are dissolved in a beaker containing 15 g of $H_2O$ acidified with 0.5 ml of $HNO_3$ (65 wt %). After further acidification with 1.0 ml of $HNO_3$ (65 wit), 10.9 g of $Nd(CH_3COO)_3.xH_2O$ and 65 g of $H_2O$ are added (solution A).

A second solution (solution B) is prepared containing 20 g of $H_2O$ and 4.00 g of TPAOH (tetrapropyl ammonium hydroxide) (53 wt %). Solution B is added to solution A under agitation at ambient temperature and homogenized for 15 minutes. In the resultant solution the Ca:Mg:Nd atomic ratio is 13.3:53.3:33.3 (Ca/Mg=0.25).

The product obtained is dried at 120° C. for 8 hours and is then heated to 800° C. for 4 hours in an air stream.

EXAMPLE 8

8.58 g of $Mg(CH_3COO)_2.4H_2O$ and 6.30 g of $Ca(NO_3)_2.4H_2O$ are dissolved in a beaker containing 15 g of $H_2O$ acidified with 0.5 ml of $HNO_3$ (65 wt %). After further acidification with 0.3 ml of $HNO_3$ (65 wt %), 10.9 g of $Nd(CH_3COO)_3.xH_2O$ and 65 g of $H_2O$ are added (solution A).

A second solution (solution B) is prepared containing 20 g of $H_2O$ and 4.00 g of TPAOH (tetrapropyl ammonium hydroxide) (53 wt %). Solution B is added to solution A under agitation at ambient temperature and homogenized for 15 minutes. In the resultant solution the Ca:Mg:Nd atomic ratio is 26.6:40:33.3 (Ca/Mg=0.66). The product obtained is dried at 120° C. for 8 hours and is then heated to 800° C. for 4 hours in an air stream.

EXAMPLE 9 (comparative)

14.3 g of $Mg(CH_3COO)_2.4H_2O$ are dissolved in a beaker containing 15 g of $H_2O$ acidified with 0.5 ml of $HNO_3$ (65 wt %). After further acidification with 1.5 ml of $HNO_3$ (65 wt %), 10.9 g of $Nd(CH_3COO)_3.xH_2O$ and 65 g of $H_2O$ are added (solution A).

A second solution (solution B) is prepared containing 20 g of $H_2O$, 1.6 g of LiOH and 2.25 g of TPAOH (tetrapropyl ammonium hydroxide) (53 wt %).

Solution B is added to solution A under agitation at ambient temperature (about 25° C.) and homogenized for 15 minutes. In the resultant solution the Li:Mg:Nd atomic ratio is 40:40:20. The partly galled solution is left standing for 16 hours. The product obtained is dried at 110° C. for 5 hours to obtain a metal oxide mixture (lithium content 5.0 wt %) which is heated to 800° C. for 4 hours in an air stream. It is then cooled to obtain a solid with a lithium content of 3.3 wt %.

EXAMPLE 10

1.5 g of each of the catalyst precursors prepared in Examples 1 to 5 and 9 are placed in a respective fixed-bed quartz microreactor with an inner diameter of 10 mm. Methane, oxygen and helium are fed into the reactor with a methane/oxygen molar ratio of 4.0 and a methane partial pressure of 0.47 bar. The catalyst precursors are maintained at a temperature of 770° C. for 18 hours, after which the lithium content is generally of the order of 0.10 wt %. After this treatment the methane oxidative coupling test is conducted operating at a temperature of 9° C., measured by a thermocouple inserted along the catalyst bed, and at atmospheric pressure for a contact time of 0.0018 min g cat/ml (the gas volume being evaluated under normal conditions). The tests continued for 300 hours of reaction. The results are shown in Finite 1 in which the vertical axis represents the percentage yield of paraffinic and olefinic products with 2 or more carbon atoms, and the horizontal axis represents time in hours, for each of the catalysts deriving from the precursors of Examples 1–5 and 9.

| (Ex. 1 | Ca/Mg = 0.05 |
|---|---|
| Ex. 2 | Ca/Mg = 0.1 |
| Ex. 3 | Ca/Mg = 0.18 |
| Ex. 4 | Ca/Mg = 0.25 |
| Ex. 5 | Ca/Mg = 0.65 |
| Ex. 9 | Ca/Mg = 0). |

EXAMPLE 11

Figure 2:
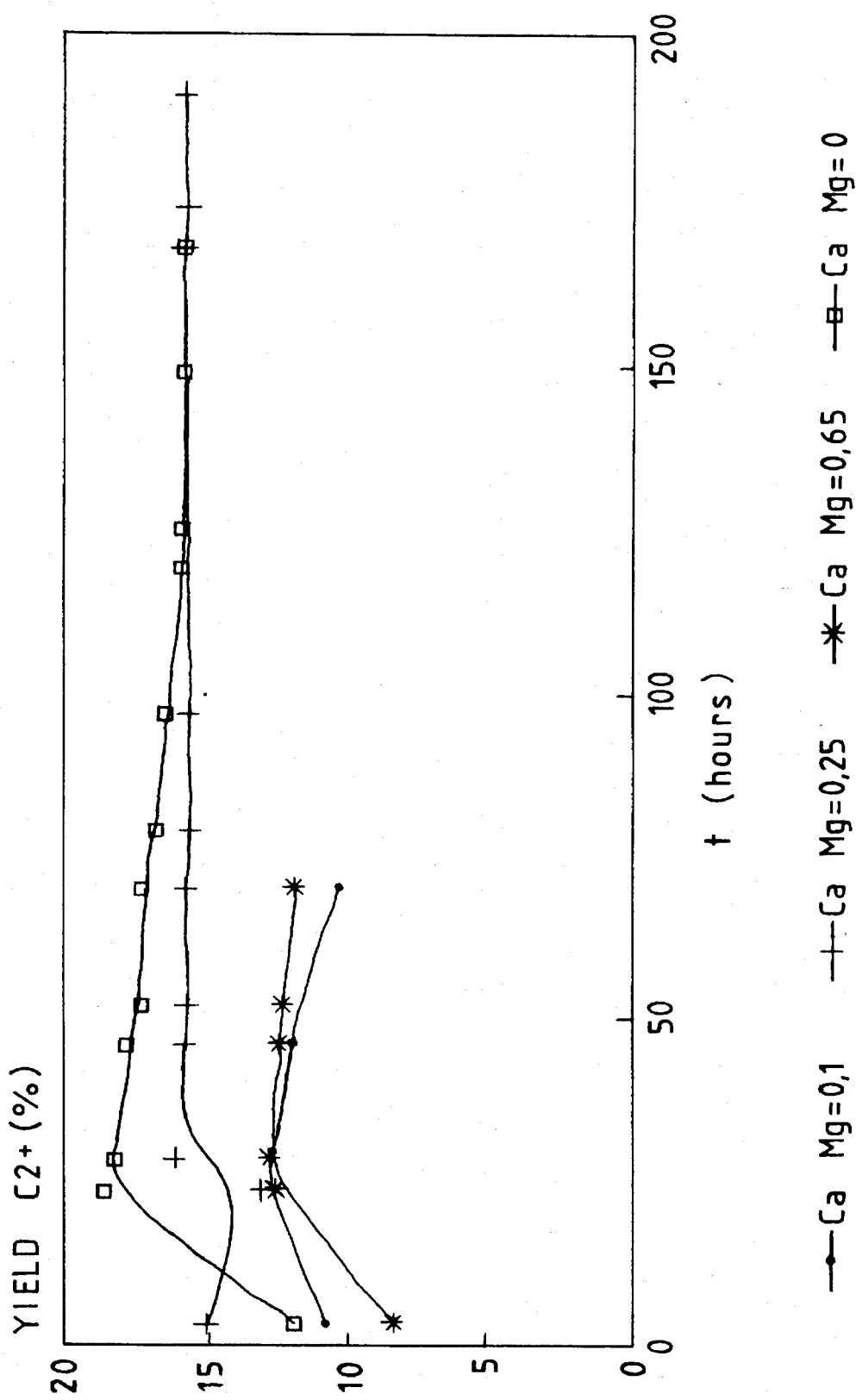

1.5 g of each of the catalysts prepared in Examples 6–8 and of the catalyst precursor of Example 9 are placed in a respective fixed-bed quartz microreactor with an inner diameter of 10 mm. Methane, oxygen and helium are fed into the reactor with a methane/oxygen molar ratio of 4.0 and a methane partial pressure of 0.47 bar. catalyst precursor of Example 9 is maintained at a temperature of 770° C. for 18 hours, after which its lithium content is of the order of 0.10 wt %. The methane oxidative coupling test is then conducted operating at a temperature of 920° C., measured by a thermocouple inserted along the catalyst bed, and at atmospheric pressure for a contact time of 0.0018 min g cat/ml (the gas volume being evaluated under normal conditions). The tests continued for 200 hours of reaction. The results are shown in FIG. 2 in which the vertical axis represents the percentage yield of paraffinic and olefinic products with 2 or more carbon atoms, and the horizontal axis represents time in hours, for each of the catalysts of Examples 6–8 and for the catalyst deriving from the precursor of Example 9

|         |              |
|---------|--------------|
| (Ex. 6  | Ca/Mg = 0.1  |
| Ex. 7   | Ca/Mg = 0.25 |
| Ex. 8   | Ca/Mg = 0.65). |

EXAMPLE 12

Long-duration tests, up to 350 hours, were conducted under different reaction conditions on the catalysts deriving from the precursors of Examples 4 and 9.

For this purpose 2.0 g are placed in the microreactor of Example 10 and treated as described in that example.

Figure 3:
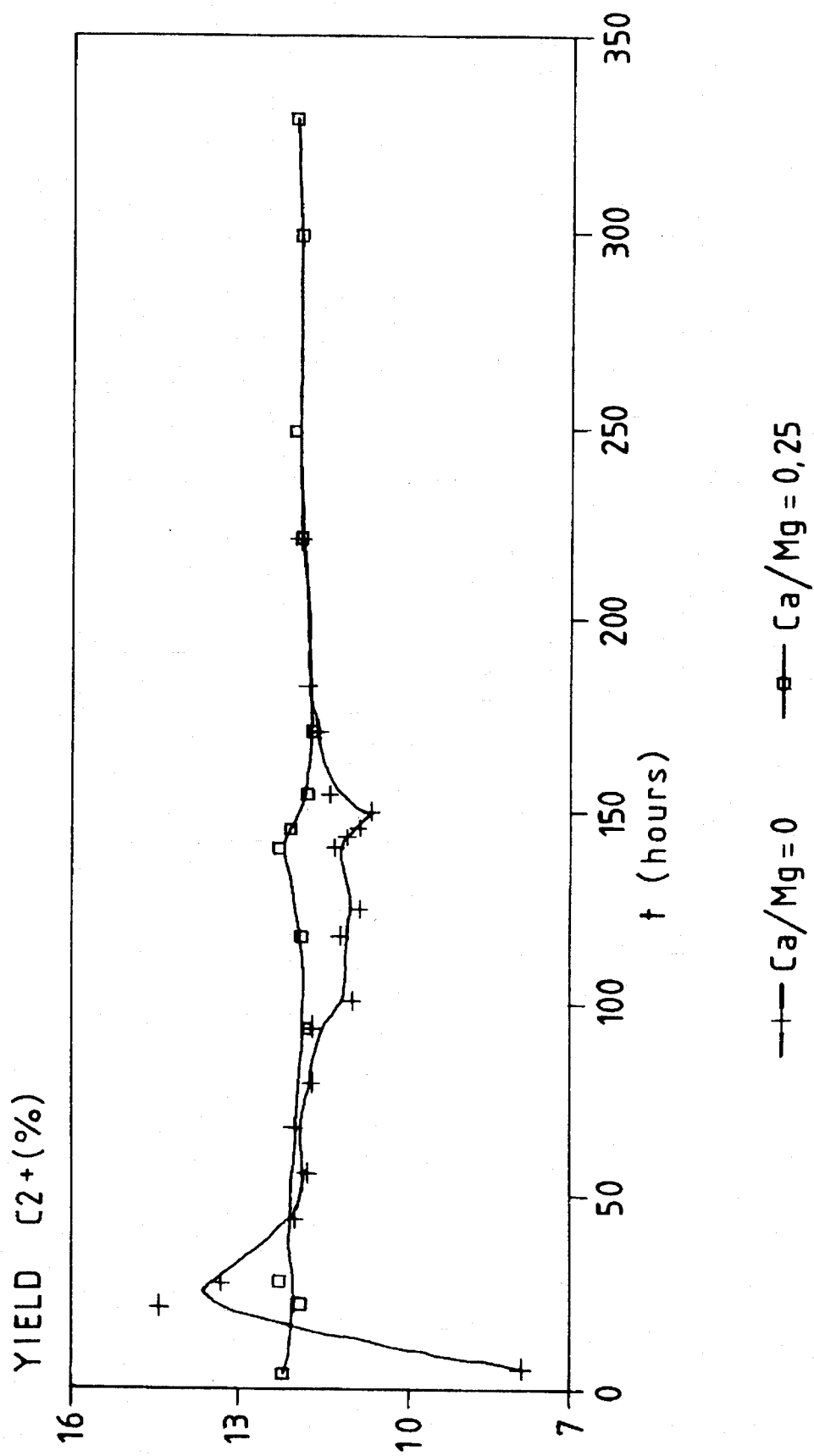

The tests were conducted by feeding methane and oxygen with a molar ratio of 7.0 and a methane partial pressure of 0.875 bar. The operating temperature was 900° C., measured by a thermocouple inserted along the catalyst bed, with a contact time of 0.0024 min g cat/ml FIG. 3 shows the variation in the percentage yield with time for each of the catalysts deriving from the precursors of Examples 4 and 9.

|        |              |
|--------|--------------|
| (Ex. 4 | Ca/Mg = 0.25 |
| Ex. 9  | Ca/Mg = 0).  |

EXAMPLE 13

A long-duration test was conducted under different reaction conditions on the catalyst 7 and on the catalyst deriving from the precursor described in Example 9.

Figure 4:
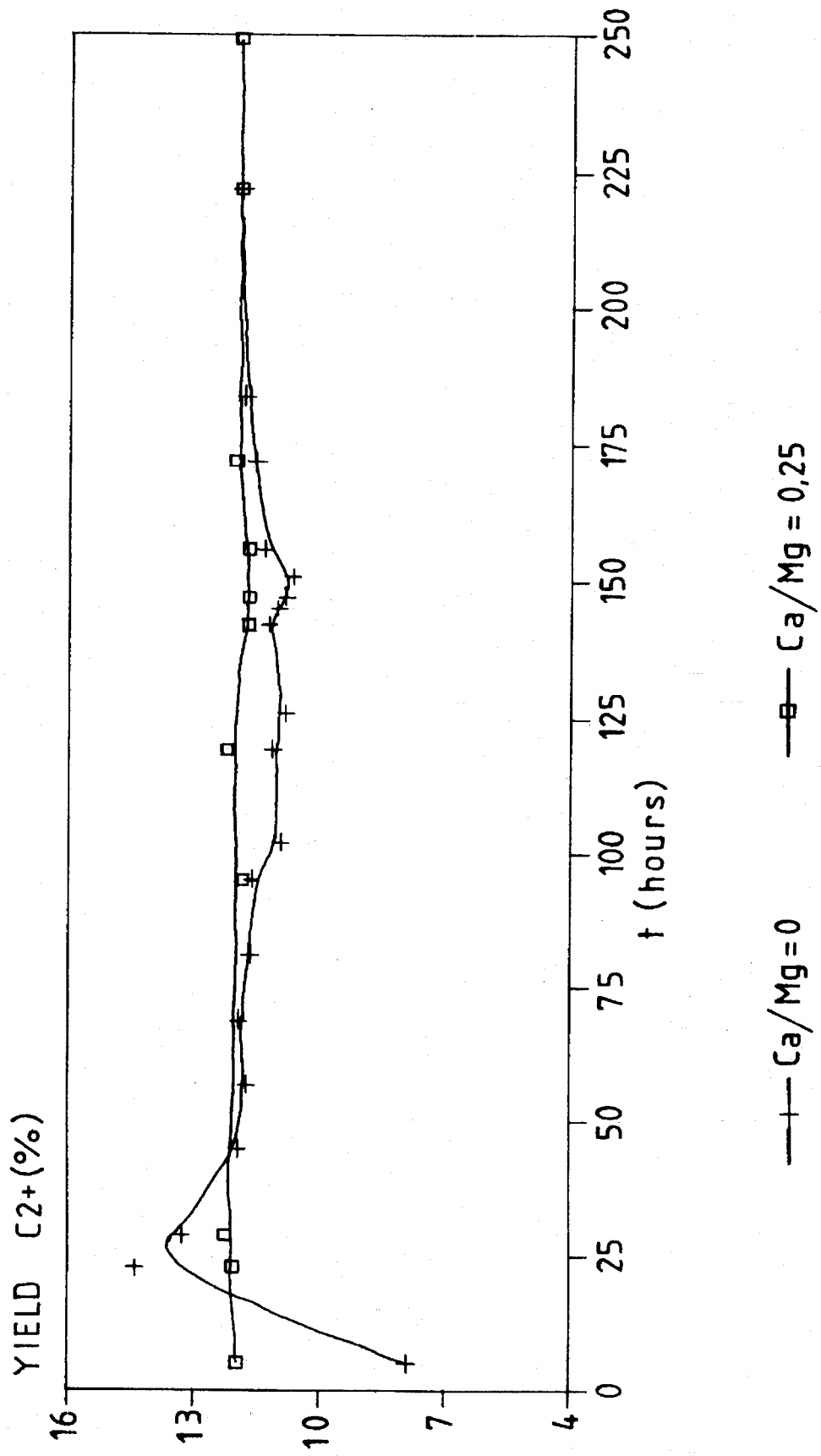

For this purpose 2.0 g are placed in the microreactor of Example 11 and treated as described in that example. The tests were conducted by feeding methane and oxygen with a molar ratio of 7.0 and a methane partial pressure of 0.875 bar. The operating temperature was 900° C., measured by a thermocouple inserted along the catalyst bed, with a contact time of 0.0024 min g cat/ml. FIG. 4 shows the variation in the percentage yield with time for the catalyst prepared in accordance with Example 7 (Ca/Mg=0.25) and for the catalyst deriving from the precursor described in Example 9 (Ca/Mg=0).

We claim:

1. A process for converting methane into higher hydrocarbon products over a metal oxide catalyst, comprising contacting a gaseous mixture containing methane and oxygen, at a temperature of at least 650° C., with a solid catalyst comprising calcium oxide, magnesium oxide, a lanthanide oxide and optionally lithium oxide, where:

in the following expressions said lithium oxide, calcium oxide and magnesium oxide are measured as lithium content, calcium content or magnesium content, respectively, by weight of the catalyst, said lithium content is between 0 and 0.20 wt %, a calcium/magnesium atomic ratio is between 0.08 and 0.7, and a (calcium+magnesium)/lanthanide atomic ratio is between 0.8/1 and 8/1.

2. The process of claim 1 wherein said lanthanide oxide is an oxide of neodymium or lanthanum.

3. The process of claim 1, in which the solid catalyst comprises calcium oxide, magnesium oxide, a lanthanide oxide and lithium oxide, wherein:

the lithium content is less than 0.20 wt %, the calcium/magnesium atomic ratio is between 0.08 and 0.7, and the (calcium+magnesium)/lanthanide atomic ratio is between 0.8/1 and 8/1.

4. The process of claim 1, in which the solid catalyst comprises calcium oxide, magnesium oxide and a lanthanide oxide, wherein:

said calcium/magnesium atomic ratio is between 0.2 and 0.4, and said (calcium+magnesium)/lanthanide atomic ratio is between 0.8/1 and 8/1.

5. A process for converting methane into higher hydrocarbon products over a metal oxide catalyst, comprising contacting a gaseous mixture containing methane and oxygen, at a temperature of at least 650° C., with a solid catalyst comprising calcium oxide, magnesium oxide, a lanthanide oxide and optionally lithium oxide, where:

in the following expressions said lithium oxide, calcium oxide and magnesium oxide are measured as lithium content, calcium content or magnesium content, respectively, by weight of the catalyst, said lithium content is between 0 and 0.20 wt %, a calcium/magnesium atomic ratio is between 0.08 and 0.7, and a (calcium+magnesium)/lanthanide atomic ratio is between 0.8 and 8, and wherein the catalyst is produced by:

preparing a mixture of lithium oxide, calcium oxide, magnesium oxide and a lanthanide oxide in which the lithium content exceeds 1 wt %; and reducing the lithium content in the mixture to less than 0.2 wt % by thermal treatment at high temperature, conducted at least partly in an oxidizing atmosphere.

6. A process for converting methane into higher hydrocarbon products over a metal oxide catalyst, comprising contacting a gaseous mixture containing methane and oxygen, at a temperature of at least 650° C., with a solid catalyst comprising calcium oxide, magnesium oxide, a lanthanide oxide and optionally lithium oxide, where:

in the following expressions said lithium oxide, calcium oxide and magnesium oxide are measured as lithium content, calcium content or magnesium content, respectively, by weight of the catalyst, said lithium content is between 0 and 0.20 wt %, a calcium/magnesium atomic ratio is between 0.08 and 0.7, and a (calcium+magnesium)/lanthanide atomic ratio is between 0.8/1 and 8/1, wherein said lithium content of an initial oxide mixture is between 4 and 10 wt % and said lithium content is reduced to a value of the order of 0.1 wt % in the final catalyst.

7. A process for converting methane into higher hydrocarbon products over a metal oxide catalyst, comprising contacting a gaseous mixture containing methane and oxygen, at a temperature of at least 650° C., with a solid catalyst comprising calcium oxide, magnesium oxide, a lanthanide oxide and optionally lithium oxide, where:

in the following expressions said lithium oxide, calcium oxide and magnesium oxide are measured as lithium content, calcium content or magnesium content, respectively, by weight of the catalyst, said lithium content is between 0 and 0.20 wt %, a calcium/magnesium atomic ratio is between 0.08 and 0.7, and a (calcium+magnesium)/lanthanide atomic ratio is between 0.8/1 and 8/1, wherein said lithium content is reduced by heating an oxide mixture in an oxygen stream or in an oxygen-containing gas stream, to a temperature generally of between 700° and 900° C., for a time generally of between 3 and 30 hours.

8. A process for converting methane into higher hydrocarbon products over a metal oxide catalyst, comprising contacting a gaseous mixture containing methane and oxygen, at a temperature of at least 650° C., with a solid catalyst comprising calcium oxide, magnesium oxide, a lanthanide oxide and optionally lithium oxide, where:

in the following expressions said lithium oxide, calcium oxide and magnesium oxide are measured as lithium content, calcium content or magnesium content, respectively, by weight of the catalyst, said lithium content is between 0 and 0.20 wt %, a calcium/magnesium atomic ratio is between 0.08 and 0.7, and a (calcium+magnesium)/lanthanide atomic ratio is between 0.8/1 and 8/1, wherein said metal oxide catalyst is produced by:

preparing a mixture of calcium oxide, magnesium oxide and a lanthanide oxide, drying this mixture and heating it to a temperature of between 650° and 1000° C. in an oxidizing atmosphere.

9. The process of claim 1, characterised in that the methane oxidative coupling reaction is effected by operating with the catalyst in the form of a fixed bed comprising feeding a gaseous stream containing methane and oxygen, optionally diluted with an inert gas, in a molar methane/oxygen ratio of between 1.5/1 and 12/1 at a temperature of between 650° and 1000° C. using a contact time of between 0.0005–0.02 minutes per gram of catalyst per milliliter of feed gas.

10. The process of claim 1 wherein said (calcium+magnesium)/lanthanide atomic ratio is between 2 and 4.

11. The process of claim 4 wherein said (calcium+magnesium)/lanthanide atomic ratio is between 2 and 4.

12. The process of claim 7 wherein the lithium is partly eliminated under said oxidizing conditions and then further oxidized in the presence of methane and oxygen, operating at a temperature between 700° and 800° C.

13. The process of claim 1, wherein said molar methane/oxygen ratio is between 2/1 and 7/1 and the temperature is between 800° to 950° C.

* * * * *